(12) United States Patent
Sidebotham et al.

(10) Patent No.: US 8,518,043 B2
(45) Date of Patent: Aug. 27, 2013

(54) MODULAR SPHERICAL HOLLOW REAMER ASSEMBLY FOR MEDICAL APPLICATIONS

(76) Inventors: Christopher G. Sidebotham, Mendham, NJ (US); Randall J. Lewis, Bethesda, MD (US)

( * ) Notice: Subject to any disclaimer, the term of this patent is extended or adjusted under 35 U.S.C. 154(b) by 1038 days.

(21) Appl. No.: 12/583,704

(22) Filed: Aug. 24, 2009

(65) Prior Publication Data

US 2010/0069908 A1    Mar. 18, 2010

Related U.S. Application Data

(63) Continuation-in-part of application No. 12/072,671, filed on Feb. 27, 2008, which is a continuation-in-part of application No. 11/973,260, filed on Oct. 5, 2007, which is a continuation-in-part of application No. 11/704,754, filed on Feb. 9, 2007.

(51) Int. Cl.
    *A61B 17/00* (2006.01)
(52) U.S. Cl.
    USPC .................................................. 606/80
(58) Field of Classification Search
    USPC ................. 606/79–81, 89, 91, 86 R
    See application file for complete search history.

(56) References Cited

U.S. PATENT DOCUMENTS

| | | | |
|---|---|---|---|
| 4,023,572 A * | 5/1977 | Weigand et al. | 606/81 |
| 4,116,200 A | 9/1978 | Braun et al. | 605/81 |
| 4,686,080 A * | 8/1987 | Hara et al. | 419/8 |
| 4,811,632 A | 3/1989 | Salyer | 76/115 |
| 5,100,267 A | 3/1992 | Salyer | 407/54 |
| 5,116,165 A | 5/1992 | Salyer | 407/54 |
| 5,171,312 A | 12/1992 | Salyer | 606/81 |
| 5,171,313 A | 12/1992 | Salyer | 606/86 |
| 5,236,433 A | 8/1993 | Salyer | 606/91 |
| 5,282,804 A | 2/1994 | Salyer | 606/86 |
| 5,299,893 A | 4/1994 | Salyer | 407/54 |
| 5,302,234 A | 4/1994 | Grace et al. | 216/47 |
| 5,501,686 A | 3/1996 | Salyer | 696/79 |
| 5,658,290 A | 8/1997 | Lechot | 606/80 |
| 5,709,688 A | 1/1998 | Salyer | 606/81 |
| 5,755,719 A | 5/1998 | Frieze | 606/81 |
| 5,817,096 A | 10/1998 | Salyer | 606/81 |
| 5,976,144 A | 11/1999 | Fishbein et al. | 606/80 |
| 5,976,148 A * | 11/1999 | Charpenet et al. | 606/91 |

(Continued)

FOREIGN PATENT DOCUMENTS

WO    WO/9007908    7/1990

*Primary Examiner* — Kevin T Truong
*Assistant Examiner* — Michael Araj
(74) *Attorney, Agent, or Firm* — Ernest D. Buff; Ernest D. Buff & Assoc. LLC; Dave Narasimhan (57) ABSTRACT

A low cost disposable spherical hollow reamer for medical applications includes a reusable shaft and a disposable spherical hollow reamer. The hollow reamer is thin sheet metal with 0.125 mm to 0.812 mm thickness and has plurality of cutters and apertures that extend through its thickness. The shaft has a proximal end for attachment to a drill and a distal precision threaded screw end. The spherical hollow reamer has welded first plate in its interior with a precision threaded aperture engaging with the threaded end of the reusable shaft. The spherical hollow reamer has a welded second plate with a central precision aperture that slides over the shaft external surface. The threaded attachment and sliding fit attachment provides wobble free reaming action. The welded second plate in combination with the interior surface of the spherical hollow reamer forms enclosed space for capturing bone fragment and bone cement debris.

15 Claims, 7 Drawing Sheets

(56) References Cited

U.S. PATENT DOCUMENTS

| | | | |
|---|---|---|---|
| 5,980,170 A | 11/1999 | Salyer | 408/239 R |
| 6,001,105 A | 12/1999 | Salyer | 606/81 |
| 6,168,600 B1 | 1/2001 | Grace et al. | 606/81 |
| 6,409,732 B1 | 6/2002 | Salyer | 606/91 |
| 6,428,543 B1 | 8/2002 | Salyer | 606/81 |
| 6,730,094 B2 | 5/2004 | Salyer et al. | 606/80 |
| 6,875,217 B2 | 4/2005 | Wolford | 606/81 |
| 6,951,563 B2 | 10/2005 | Wolford | 606/81 |
| 6,978,648 B2 | 12/2005 | Wolford | 72/74 |
| 7,074,224 B2 * | 7/2006 | Daniels et al. | 606/80 |
| 7,220,264 B1 * | 5/2007 | Hershberger | 606/81 |
| 2003/0181916 A1 | 9/2003 | Wolfdord | 606/81 |
| 2004/0073226 A1 * | 4/2004 | Cotting et al. | 606/91 |
| 2005/0049601 A1 * | 3/2005 | Keller | 606/81 |
| 2006/0095041 A1 | 5/2006 | Fehlbaum et al. | 606/81 |
| 2006/0106393 A1 * | 5/2006 | Huebner et al. | 606/80 |
| 2006/0235539 A1 | 10/2006 | Blunn et al. | 623/22.12 |
| 2008/0243124 A1 | 10/2008 | Fehlbaum et al. | 606/80 |
| 2009/0088757 A1 | 4/2009 | Tulkis | 606/81 |
| 2009/0163921 A1 | 6/2009 | Lechot et al. | 606/81 |

* cited by examiner

MODULAR SPHERICAL HOLLOW REAMER ASSEMBLY FOR MEDICAL APPLICATIONS

This is a Continuation-In-Part of application Ser. No. 12/072,671, filed on Feb. 27, 2008 for "Modular spherical hollow reamer assembly for medical applications" which is a Continuation-In-Part of application Ser. No. 11/973,260, filed Oct. 5, 2007 for "Modular Tapered Hollow Reamer For Medical Applications" which, in turn, is a Continuation-In-Part of application Ser. No. 11/704,754, filed Feb. 9, 2007, the disclosures of which are hereby incorporated in their entirety by reference thereto.

BACKGROUND OF THE INVENTION

1. Field of the Invention

The present invention relates to a modular easy-to-assemble low cost sheet metal formed disposable modular spherical hollow reamer assembly for medical applications that has a bone fragment and bone debris capturing cavity, and can be attached concentric to a reusable shaft.

2. Description of the Prior Art

Reaming of the internal canal of bones is required in many surgical procedures of orthopedic surgery. These procedures include hip replacement and shoulder replacement, and the like. Reamers are used in procedures that involve creation of acetabular bone cavities that accept a properly sized acetabular cups. Prior art reamers typically fall into two major classes: rigid and flexible shaft. Typically, reaming of the internal bone cavity is achieved through utilization of a spherical reamer some having provisions for discharging and collecting reamed bone fragments. Spherical reamers currently utilized are required to cut both cancellous bone (spongy bone) and cortical bone (hard bone). Cortical bone is generally denser and stronger, requiring an efficient cutter to machine the acetabular cavity for a proper fit of the acetabular cup. Conventional spherical reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. These prior art solid spherical reamers are intended for multiple uses and therefore become less efficient after each surgery, resulting in poor cutting performance and bone necrosis. These dull blades also incorporate bone debris or bone cement debris into the living bone tissue, creating bone healing problems and fixation of an implanted acetabular cup.

U.S. Pat. No. 4,116,200 to Braun et al. discloses a milling tool for surgical purposes. This surgical milling tool is operated with a hand-operated milling machine for milling the heads or sockets of bone joints of a spherical shape. The tool is formed of a hemispherical cup integrally formed with a cylindrical skirt and flange and is provided with a plurality of openings of semi-oval shape, each having a cutting edge arranged at the minor axis of the oval shape. The openings are situated such that, upon rotation of the cup, the cutting edges thereof overlap to provide a continuous cutting edge surface conforming generally to the shape of the cup. The formation of fine bone shavings is avoided by use of this milling tool. The surgical milling tool utilizes a integrally formed hemispherical cup having a plurality of openings appointed with cutting edges for milling sockets of bone joints. The hemispherical shape of cup provides the ability to hollow out the arcuate shape of the bone joints. Bone and cartilage shavings are formed during the milling process and are collected in a border area inside of the hemispherical cup. The surgical milling tool is provided for multiple use and is not a disposable spherical hollow reamer, and therefore the tool will become less efficient after each surgery, resulting in poor cutting performance and bone necrosis.

U.S. Pat. No. 4,811,632 to Salyer discloses surgical reamer. a method of producing an acetabular reamer cup. This method comprises the steps of fabricating a bowl-shaped cup-blank having an outer surface, an inner surface and a rim, perforating a plurality of holes through the cup-blank, the holes each being surrounded by a margin, deforming outwardly a cutting portion of the margin of each of the holes, smoothing the outer surface of the cup-blank to sharpen the deformed cutting portions, raising cutting edges from the cutting portions and removing the rim. The cutting edges are disposed to cut upon rotation of the acetabular reamer. The cup manufactured by this method is preferred because of its improved strength and consistently superior cutting edges. The acetabular reamer utilizes a hemispherical or bowl-shaped cup having a spherical construction and a plurality cutting openings for milling sockets of joints. The hemispherical shape of reamer provides the ability to hollow out the arcuate shape of the bone joints. The acetabular reamer is provided for multiple use, and therefore the tool will become less efficient after each surgery, resulting in poor cutting performance and bone necrosis.

U.S. Pat. No. 5,100,267 and its continuation in part U.S. Pat. No. 5,299,893 to Salyer disclose a disposable acetabular reamer cup. The disposable acetabular reamer cup has a cutting bowl having a plurality of cutting edges. The cutting bowl has perforations adjoining the cutting edges. The cutting bowl defines an axis of rotation. The cutting bowl has a bottom opening. A transparent polymeric plug is joined to the cutting bowl. The plug is concentric with the axis of rotation. It occupies the bottom opening; and has a tool driver opening concentric with the axis of rotation. When a torque is applied, the bowl is turned with respect to the plug, which means that the cutting torque is transmitted through the plug and transferred to the cutting plug through the detents. There is no direct connection between the shaft and the cutting bowl other than through the plug. Concentricity of the cutting bowl with respect to that of the shaft is therefore not assured.

U.S. Pat. No. 5,116,165 to Salyer discloses an acetabular reamer cup. This acetabular reamer cup comprises a cutting bowl having a plurality of singly curved cutting edges. The cutting bowl has a plurality of slots preceding the cutting edges. The cutting bowl defines an axis of rotation. A bottom is joined to the cutting bowl. The bottom has a tool driver opening concentric with the axis of rotation. With a right handed acetabular reamer cup that cuts when pressed against a substrate and rotated in a clockwise direction, slots are positioned to the right of respective cutters. There is no direct connection between the shaft and the cutting bowl other than through the base aperture. The concentricity of the cutting bowl with respect to that of the shaft is therefore not assured.

U.S. Pat. No. 5,302,234 to Grace, et al. discloses surgical cutting instrument forming method. This surgical cutting instrument is a sheet metal tool that is not planar, and the tools is made from a sheet metal blank, which has a first surface and an opposing second surface. A etching resistant material is applied to the first surface and etched by a chemical etching agent to form a sharp edge that terminates on the second surface coated with a etch resistant material. There is no indication how this non planer chemically etched tool is mounted concentrically on a shaft.

U.S. Pat. No. 5,658,290 to Lechot discloses an assembly comprising reamer spindle and reamer for surgery. The reamer comprises a cap and at least three radial rods which are arranged uniformly on the inside edge of the cap and join up integrally at the center of the cap. The reamer spindle comprises a shank on which there is fixed a reamer spindle head that is equipped with a bayonet with locking means for the securing of the reamer. The securing catches of the bayonet are intended to receive the radial rods of the reamer. The connection between the reamer rods and bayonet does not provide a precise centerline matching arrangement.

U.S. Pat. No. 5,709,688, as well as U.S. Pat. Nos. 6,001, 105, and 6,428,543 to Salyer disclose an acetabular reamer cup and method of producing the same. This method for making an acetabular reamer cup for an acetabular reamer comprises the steps of: fabricating a bowl shaped cup-blank having outer and inner bowl shaped surfaces, perforating a plurality of holes through the cup-blank, the holes each are surrounded by a curved margin, deforming outwardly of the outer surface a cutting portion of the margin of each of the holes, thereby forming cutting edges, the cutting portions are curved outwardly of the outer surface, the cutting edges are curved tangentially of the outer surface and disposed to cut upon rotation of the acetabular reamer. An acetabular reamer cup is also provided with a cutting bowl having a plurality of curved cutting edges. The cutting bowl has a plurality of openings preceding the cutting edges, and a generally conical rise following the cutting edges. The cutting edges are spirally arranged about the axis of rotation of the cutting bowl, and a bottom adjoined to the cutting bowl. The bottom has a tool driver opening coaxial with the cutting bowl and the cutting edges. Bone debris collection compartment is located directly below the actabular reamer. Bottom of the acetabular reamer has a tool driver opening, which is concentric with the cutting bowl. The driver opening engages with the shaft, which drives the acetabular reamer. This form of attachment of the shaft with the acetabular reamer does not ensure alignment of axis of the shaft with that of the acetabular reamer. The acetabular reamer is not indicated to be disposable.

U.S. Pat. No. 5,755,719 to Frieze, et al. discloses an acetabular reamer. This acetabular reamer includes a base, a first set of semi-circular blades attached to the base, and a second set of semi-circular blades also contacting said base, and crossing and intersecting with said first set of blades at right angles thereto. The base preferably comprises a circular plate having a hexagonal drive hole in the center thereof and a plurality of slots in the periphery thereof for anchoring the blades. Each semi-circular blade includes a first end having a projection thereon, a second end opposite from said first end and also having a projection thereon, a first edge having serrated cutting teeth thereon, a second edge opposite from said first edge, and a first and second side surface. The cutting edge of the first set of blades includes a plurality of outwardly facing slots, which mate with and engage a second set of inwardly facing slots in the second edge of said second blades. When the first and second set of blades are assembled in this fashion the cutting edges of both sets of blades lie in the same spherical plane. The projections can comprise snap-in projections that automatically lock in position or projections that can be twisted and locked into position. Alternatively, the base can comprise a pair of upper and lower plates with apertures in the upper plate such that when the blade projections mate with the apertures, riveting of the lower plate with respect to the upper plate locks the projections and their related blades into position on the base. When the reamer is assembled it has a hemispherical shape suitable for reaming the acetabulum of the hip so that the acetabular portion of a hip implant properly fits into the acetabulum. The acetabular reamer is an open structure and the bone fragments will migrate back into the cutting zone, since no containment space is formed by the open structure of the cutter blades inserted into the base. The drive shaft is coupled to a hexagonal aperture in the base plate. This method of attachment does not align the hemispherical cutter centerline with that of the drive shaft. As such, the arrangement causes wobbliness of the cutter in the bone cavity.

U.S. Pat. No. 5,976,144 to Fishbein et al. discloses a hollow dome reamer with removable teeth. This surgical reamer has a hollow dome with apertures spaced apart arranged in arcs extending from an apex of the dome to the base portion of the dome. Removable teeth are positioned in the apertures. Each cutting tooth has a flange that is aligned flush with the external surface of the dome, and a raised cutting edge extending above the flange and the external surface of the dome. An interior passageway communicates between the outside and inside of the dome. A base plate is removably secured on the base portion of the dome to provide closure of the central cavity of the dome. A perspective view of the cutter of the reamer is shown hereinbelow on the left; a perspective view of the reamer with removable, replaceable cutters is shown herein on the right. The base plate is secured to the dome by retaining springs. A drive shaft is connected to the base plate through an aperture in the base plate and held in place by a spring. The surgical reamer has a hollow dome with apertures spaced apart appointed to receive removable teeth positioned therein. Although the teeth are removable, they are not disposable in nature; the teeth are removed for replacement or for re-sharpening and are used again. The dome is connected to a base plate, which is further connected to a shaft member and retained by a spring clip and an interlocking latch. There is no direct attachment of the shaft to the dome and this multitude of connections to the shaft does not assure that the centerline of the shaft coincides with that of the hollow dome.

U.S. Pat. No. 5,980,170 to Salyer as well as U.S. Pat. Nos. 5,817,096, 5,501,686, 5,282,804, 5,236,433, 5,171,313, 5,171,312 disclose a tool driver. This tool driver has a shaft with a longitudinal axis and opposite ends. A boss is secured at one of said shaft ends by which the tool driver is connected to a rotary tool. A tool collate is secured at the other of the shaft ends by which the tool driver may be driven by a surgical hand piece having a chuck in which the collate may be positioned. The boss has a distal end surface with a groove therein. Both the groove and the distal end surface extend transversely of the axis. A pin is positioned in the groove on the axis. A latch mechanism is provided to hold a mounting bar of a rotary tool in the groove on the pin, whereby the rotary tool is held exactly coaxially of the driver during use. The rotary tool, which is used with the driver has a bar which has the same dimensions as the groove in the boss of the tool driver of the invention. The bar thus fills the slot and is complementary to the slot. The bar has a hole therein which is complementary to the pin. The pin extends coaxially of the shaft and the boss. The bar hole in which the pin of the tool driver is positioned is precisely coaxial of the axis of the tool about which the cutting edges are precisely positioned. The tool driver has a shaft appointed to receive acetabular reamer cups and patella cutters. The cutters are appointed to be connected to the tip of the shaft by means of mounting bar in the cutter and a slot in the shaft secured by a complementary pin. This method of attachment—using a mounting bar that slides into a slot—does not align the centerline of the shaft with that of the reamer.

U.S. Pat. No. 6,168,600 to Grace, et al discloses an acetabular reamer backing plate and method of use. The backing plate for an acetabular reamer assembly that has a planar surface allows for the attachment of a reamer driver. The rigid backing plate terminates in an outer circumferential edge, the outer circumferential edge being coupled to the peripheral bottom edge of the cutting cup. The rigid plate has an internal edge profile that has at least two finger elements protruding from the outer circumferential edge towards a central vertical axis drawn perpendicular to the planar surface of the plate form a holding opening for a reamer driver. The internal edge profile of the backing plate forms an observation opening to allow visual inspection of bone fragments. This attachment feature only uses a single point attachment of the reamer to the shaft at the edge profile of the backing plate. It is therefore subject to displacement of the shaft laterally, causing the centerlines of the shaft and reamer to be not precisely aligned.

U.S. Pat. No. 6,409,732 to Salyer discloses a tool driver. This tool driver has a shaft with a longitudinal axis and opposite ends. A boss is secured at one of the shaft ends by which the tool driver is connected to a rotary tool. A tool collate is secured to the other of the shaft ends by which the tool driver may be driven by a surgical hand piece having a chuck in which the collate may be positioned. The boss is equipped with a securing device of the bayonet type having a latch mechanism, which holds the rotary tool on the boss coaxially of the driver during use. The securing device has a tapered bore extending from the distal end of the boss axially of the shaft. The rotary tool has a diametrical bar extending across a bottom tool driver opening with a centrally located circular disk therein. The disk of the rotary tool fits within the bore of the tool shaft boss so as to concentrically locate the rotary tool and the tool shaft on the same axis. The latch mechanism holds the tool driver and the tool together in this position, whereby rotary tools of a multitude of sizes can be secured concentrically to the tool shaft without holding a plurality of critical tolerances when machining the bayonet type securing device or the rotary tool bottom bar. The tool driver is a shaft with a slot on the end that receives the acetabular reamer. It deals with the details of the device for attaching the acetabular reamer to the shaft. This type of slotted attachment does not result in coaxial mounting of the reamer that is coincident with the centerline of the shaft, even though the different components of the shaft are said to be coaxially aligned. The reamer is not indicated to be disposable.

U.S. Pat. No. 6,730,094 to Salyer et al. discloses cutting edges for reamers and a method for making same. Each reamer has a plurality of cutters spirally arranged on reamer surface. Each cutter has a continuous cutting edge. Edges may be generally straight in planes perpendicular to the reamer surface or tangential or parallel to the tangential plane with respect to the reamer surface. Cutting edges may also be curved in planes perpendicular to the reamer surface or parallel or tangential to the reamer surface. Further, the curvature may be convex, or concave or of other complex shapes. There need be no relationship between the shape of cutting edges and the shape of reamer surface. In fact, one may be curved and the other straight, or both may be curved in the same or opposite directions. These relate to the edge geometry of the cutting edges of the reamer. As explicitly stated in the summary, "It is also an advantage of the invention to provide a new and improved reamer that can be stripped in the field and sterilized for re-use, and which does not have crevices and other structures to hold bone chips and tissue which cannot be easily dislodged prior to sterilization", the reamer is intended to be reused after sterilization and is not a disposable spherical reamer.

U.S. Pat. No. 6,875,217 to Wolford discloses an orthopedic reamer assembly. This orthopedic reamer assembly includes a reamer with a generally hemispherical shell having a concave side and at least one attachment feature associated with the concave side. A driver is attachable to the reamer and has a shaft with a reamer end. A releasable collar is disposed on the reamer end, which includes a boss having at least one retaining pin. A sleeve is fitted over the boss and includes a groove that is proximate to a corresponding retaining pin. The reamer has a cavity in the reamer end with a biasing element. The biasing element biases the sleeve in a closed position respective to the boss. A release pin, which press fits into the sleeve is provided in the reamer end, and is conveyed through the cavity, with the biasing element biasing against the release pin. The orthopedic reamer assembly is a complicated attachment of design of the drive shaft to an acetabular reamer with multiple sliding parts. Since each of the sliding parts requires a sliding fit, there are inherent displacement possibilities and therefore, the centerline of the shaft is not reliably aligned with the centerline of the acetabular reamer. Moreover, the acetabular reamer is not indicated to be a disposable spherical hollow reamer and requires complicated machined elements to enable a sliding fit.

U.S. Pat. No. 6,951,563 to Wolford discloses orthopaedic reamer with flat cutting teeth. An orthopaedic reamer for cutting bone includes a shaft and a head coupled with the shaft. The head includes a distal face with a plurality of punched cutting teeth. Each cutting tooth includes a hole extending through the head. At least a portion of each hole has a substantially round perimeter. A raised lip is positioned adjacent to and extends around at least part of the substantially round portion. A reamer-to-shaft attachment that has concentricity is not disclosed.

U.S. Pat. No. 6,978,648 to Wolford discloses an acetabular reamer lipping system and method. This is a lipping tool for lipping an acetabular reamer. The lipping tool has a bending form with a curved surface and a bending form axis of rotation. A pressure tool has a pressure tool curved surface adjacent to and complimentary with the bending form curved surface. The pressure tool has a pressure tool axis. The pressure tool is rotatable about the pressure tool axis and is also rotatable about the bending form axis. This lipping tool merely bends a spherical hollow reamer into shape and does not disclose how this lipped reamer is attached concentric to a shaft that rotates the reamer.

U.S. Patent Application Publication No. 2003/0181916 to Wolford discloses an orthopedic reamer with flat cutting teeth. This orthopedic reamer is for cutting bone and includes a shaft and a head coupled with the shaft. The head includes a distal face with a plurality of cutting teeth. Each cutting tooth includes a hole extending through the head. At least a portion of each hole has a substantially round perimeter. A raised lip is positioned adjacent to and extends around at least part of the substantially round portion. The '916 publication discloses an orthopedic reamer with flat cutting teeth having a shaft attached to acetabular reamer cups. The reamer cups of the '916 publication are not disposable in nature. The orthopedic reamer with flat cutting teeth publication does not provide a spherical hollow reamer assembly including a space for capturing bone fragments or bone cement debris. The attachment of the acetabular reamer to the drive shaft includes a complicated mechanism and does not reliably align the centerline of the drive shaft with that of the acetabular reamer. As such, wobble free rotation is not provided.

U.S. Patent Application Publication No. 2006/0095041 to Fehlbaum et al. discloses a contoured reamer teeth and method for their manufacture. An acetabular reamer has a cutting shell having a series of doubly curved cutting teeth of a quantity to substantially reduce a cutting pressure on each tooth as well as to reduce a size of a typical chip generated upon cutting. Substantially all the teeth each have a matched arc cutting edge of substantial length that has a cutting profile which substantially matches a profile of a shape to be cut. The apertures in which the cutting edges are formed from a sheet material and have at least one flat edge formed by a punch. Such a configuration reduces the number of teeth required to cut the shape. The contoured reamer teeth publication does not provide a procedure for assembling a reamer. In addition, the contoured reamer teeth are not disposable in nature, and therefore over time will become dulled, thereby causing enhanced friction during reaming and potentially damaging the bone.

U.S. Patent Application Publication No. 2006/0235539 to Blunn et al. discloses a surgical kit for hemiarthroplasty hip replacement. This kit comprises a femoral head and a reamer. The kit is suited for performing a hip hemiarthroplasty, in which a femoral head is fitted directly into a socket reamed into the acetabular without any permanent liner or prosthetic acetabular being implanted. The reamer is used to ream out the acetabulum until cancellous bone is exposed so that it bleeds liquid containing stem cells. The spherical shape of reamer provides the ability to hollow out the arcuate shape of the bone joints. The surgical kit disclosed by the '539 publication is provided for multiple use, and therefore the tool will become less efficient after each surgery, resulting in poor cutting performance and bone necrosis. Significantly, the '539 publication does not teach a disposable spherical hollow surgical reamer tool that is attached to a drive shaft with coincident centerlines.

U.S. Patent Application Publication No. 2008/0243124 to Fehlbaum, et al. discloses contoured Reamer Teeth and Method of Manufacture. An acetabular reamer is designed for cutting a required cut shape. The reamer has a cutting shell having a series of doubly curved cutting teeth of a quantity to substantially reduce a cutting pressure on each tooth as well as to reduce a size of a typical chip generated upon cutting. Substantially all the teeth each have a matched arc cutting edge of substantial length that has a cutting profile which substantially matches a profile of a shape to be cut. The apertures in which the cutting edges are formed have at least one straight edge by which a punch may be used in the process of forming the oriented edge. This disclosure deals with preparing cutting edges by first forming apertures with one flat edge using a laser in a spherically formed sheet and using a punch against the flat edge to create a cutting edge. There is no disclosure in the application regarding the concentric attachment of a reamer with a shaft.

U.S. Patent Application Publication No. 2009/0088757 to Tulkis discloses an acetabular reamer. The reamer assembly includes a tool driver and a tool. Tool driver comprises a shaft. The tool receiving end of the shaft has a flange. Formed in the flange are four L-shaped bayonet catches, which receive the tool. The tool has a body having slots. A cutter can slidably fit into the slots. When installed in the slots, the cutters project slightly above the body. The projecting portions of the cutters form the cutting edges for shaving or cutting tissue. The reamer is formed by attaching a tool to the tool driver by lowering it in the L-shaped bayonet catches. The reamer can be coupled to a drive means such as a hand drill and inserted in a body cavity. Operating the reamer against body tissue shaves of body tissue. This type of four L-shaped bayonet catches attaching a shaft to a reamer does not provide precise alignment of the centerline of the reamer and shaft since it is a single location attachment.

U.S. Patent Application Publication No. 2009/0163921 to Lechot et al. discloses disposable acetabular reamer from flat stock. This disposable reamer has a reamer assembly that includes a rigid, circular molded biocompatible plastic base with an interface for mating with a holder and a press-formed, thin walled, perforated and toothed cutting body having interlocking interfaces for locking with the base. The base has an aperture 19 for attachment to a shaft. This form of attachment is a single point attachment to a deformable plastic body and will not maintain a precise alignment of the centerline of the shaft and that of the reamer especially after use when the polymer base aperture deforms.

Foreign Publication No. WO 9007908 to Schelhas discloses an acetabulum reamer. Acetabulum reamer for reaming the acetabulum of the human pelvic bone prior to insertion of an artificial hip joint cup comprises a reamer head on a shaft and a spiral reaming ridge arranged about the axis of the shaft and provided with reaming devices. The outer edge of the reaming ridge is delimited by a section of a spherical surface whose axis of rotation is flush with the axis of the shaft. The acetabulum reamer utilizes a spherical head for reaming a socket in an acetabulum. The spherical shape of reamer provides the ability to hollow out the arcuate shape of the bone joints. The reamer is provided for multiple use, and therefore the tool will become less efficient after each surgery, resulting in poor cutting performance and bone necrosis. Significantly, the acetabulum reamer publication does not teach a disposable spherical hollow surgical reamer tool that is attached to a drive shaft with coincident centerlines.

There remains a need in the art for a modular easy-to-assemble spherical hollow reamer for medical applications having a disposable spherical hollow cutter. Also needed in the art is a disposable spherical hollow cutter assembly of the type described, which can be attached concentric to a reusable shaft portion that provides means for reaming of an acetabular bone cavity in bones without any wobbly movement. Further needed in the art is a cutter assembly having means for collecting bone debris and keeping the collected debris displaced from the cutting portion, so that heat generated at the bone cutting surface is minimized. Still further needed in the art is a spherical hollow reamer assembly wherein, after one use of the spherical hollow reamer, a new spherical hollow cutter with sharp fresh cutting edges can be utilized and the old hollow cutter can be discarded.

SUMMARY OF THE INVENTION

The present invention provides a modular easy-to-assemble low cost spherical hollow reamer for medical applications having a disposable spherical reamer fabricated from a sheet material that is concentrically attached to a reusable shaft portion. The attachment between the disposable spherical hollow reamer and the reusable shaft is accomplished by a precision threaded screw attachment at one end and a support feature at a distance away from the first threaded attachment location. The disposable spherical hollow reamer has in its interior a first welded plate that has a central threaded aperture with precision machined screw threads, and which connects directly into a threaded portion provided at the distal end of the reusable shaft. This forms the first precise attachment location between the reusable shaft and the spherical hollow reamer. These threads typically have fine threads with 8 to 12 threads per inch, preferably ACME threads similar to that present in a precision micrometer. Since these threads are formed during the machining of both the shaft and machining of the plate welded to the spherical hollow reamer, their centerlines are precisely aligned when the spherical hollow reamer is threaded into the distal end of the reusable shaft. The second attachment point is a second welded plate with a central aperture that is displaced at a distance from the first welded plate. The central aperture is concentric with the axis of the spherical hollow reamer and is machined with a tolerance fit that allows this second welded plate of the spherical hollow reamer to slide over the precisely machined outer diameter surface of the shaft, providing a second support location. Several sizes of reamers have identical second plate aperture and first plate threads, and they can be interchangeably attached to several spherical hollow reamers providing interchangeability.

Briefly stated, the spherical hollow reamer has a second plate welded at the distal circumference end of the spherical hollow reamer away from the first threaded welded plate. The second welded plate has a central aperture that closely fits the shaft outer diameter during assembly. The fit class is a close sliding and therefore this spherical hollow reamer is attached to the shaft first at the threaded location and secondly by the sliding fit between the shaft outer surface and the aperture of the second welded plate, which is displaced from the first attachment point. These two attachment points create a unique mechanical arrangement wherein the centerline of the shaft and the centerline of the spherical hollow reamer and this centerline match are perfectly matched even when high cutting loads are applied. Thus, when the proximal end of the reusable shaft is inserted into a drilling machine and the shaft is rotated, the disposable spherical hollow reamer rotates without any wobbliness and reams or cuts a precise bone cavity replicating the shape of the spherical hollow reamer.

Cutting teeth and bone fragment discharging apertures are provided on the outer surface of the spherical hollow cutter. The spherical hollow reamer has an end plate with a central aperture welded integral with the outer edges of the spherical hollow reamer. When the shaft is screwed into the threads of the spherical hollow reamer the outer surface of the shaft slides in the welded end plate aperture thereby creating an enclosed space within the spherical hollow reamer for accumulation of bone debris or bone cement debris. The quick removal of bone fragments or bone cement debris reduces the amount of heat generated during the cutting/reaming procedure. Graduations are provided in the reusable shaft portion to determine the depth of insertion of the spherical hollow reamer into the bone cavity.

Generally stated, the Hollow Spherical Reamer for Medical Applications broadly comprises: (i) a reusable shaft portion having a threaded distal end, a proximal end for coupling with a drilling machine and a central region for a plate; (ii) a disposable spherical reamer portion with a plurality of cutting teeth and apertures for discharging bone and bone cement fragments; (iii) said disposable hollow reamer having a precisely machined screw element on a welded first plate at an interior location of the spherical hollow reamer for the screwed attachment of the hollow spherical reamer to the reusable shaft distal end; (iv) said spherical hollow reamer has a second welded end plate at or near the circumferential end of the spherical hollow reamer and having a precisely machined central aperture that can slide over the outer surface of the shaft during assembly; (v) said second welded plate creating a bone debris and bone cement debris collection space within the spherical hollow reamer; and (vi) said proximal region of the reusable shaft having a coupling portion for attachment to a drilling device. The modular spherical hollow reamer of the present invention solves the problems associated with the prior art reamers. In accordance with the present invention, the modular spherical hollow reamer for medical applications has an easy-to-assemble disposable low cost hollow spherical reamer, which can be attached to a reusable shaft that allows for a fresh reamer to be used with each new application of the reamer. The modular spherical hollow reamer of the present invention transfers shaft torque reliably through the screwed connection while at the same time maintains the centerline of the spherical reamer preventing wobbliness thereof during cutting. Bone and bone cement fragments are collected and stored away from the bone cutting area thereby reducing the possibility of bone fragment incorporation into living bone tissue. The modular spherical hollow reamer gradually creates the acetabular bone cavity or resizes an existing acetabular bone cavity, thereby reducing heat during its surgical usage. Owing to the presence of these features, the modular spherical hollow reamer of this invention is safer to use and operates more efficiently than prior art reamers.

The process for manufacturing the low cost spherical hollow reamer that is disposable involves the following steps:
1. The hollow cutter is made from flat sheet stock of 17-4 stainless steel or 420 stainless steel with a sheet thickness of 0.005 inch to 0.039 inch that is individually stamped to a geometrical shape as a hemi-spherical body or stamped into a plurality of petals or shapes that can be bent and joined together to a hemi-spherical shape by laser welding that adds no additional material;
2. The plurality of cutting teeth and optionally plurality of apertures for removing the bone fragments from the cutting interface of the low cost spherical hollow reamer preferably may be punched prior to bending and welding or after bending and welding.

The Spherical Hollow Reamer Assembly is adapted to be utilized when preparing bone cavities that receive acetabular cups in a close fitting configuration with precise cavity geometry. The cavities may be prepared from a previously prepared bone cavity in which the acetabular cup has come loose and has to be replaced. In this case, the bone cavity is enlarged and the bone cement previously used has to be completely reamed out and removed. The Spherical Hollow Reamer Assembly may also be used to create a bone cavity on a bone section that has no previously installed acetabular cup. The spherical hollow reamer is disposable, so that the cutting performance of the device is not compromised through repeated use. Several of the clinical problems encountered with conventional reamers are overcome through utilization of the Spherical Hollow Reamers Assembly. Novel design features of the Spherical Hollow Reamer Assembly and improvements to conventional reamers are multifaceted, and include a reusable shaft with a precision threaded distal end adapted to receive a disposable, single-use spherical hollow reamer portion with a corresponding precision threaded central screw providing a center line aligned wobble free attachment of the reamer. The threading on the distal end of the shaft and the mating screw element have a clockwise thread that self-tightens upon use. The spherical hollow reamer portion is discarded after a single use to ensure a sharp cutter for use in surgery. Moreover, when dealing with revision acetabular cup surgery, spherical hollow reamers have also been designed to cut bone cement [Polymethylmethacrylate (Acrylic) or PMMA] in a more efficient manner by providing internal space to capture the debris. This reduces both the cutting temperature and time required to remove the remnant cement mantle. Each of these features operates to decrease heat to the bone and reduce operating room time required for acetabular cup revision surgery.

BRIEF DESCRIPTION OF DRAWINGS

The invention will be more fully understood and further advantages will become apparent when reference is had to the following detailed description of the preferred embodiments and the accompanying drawings, in which.

DESCRIPTION OF THE PREFERRED EMBODIMENTS

In orthopedic surgery, total hip replacements require reaming the internal geometry of the acetabulum in order to establish a precise fit for the implant. This preparation can be intended for either cementing an acetabular cup (preparation would be oversized to the implant) or press fitting an acetabular cup (preparation undersized to the implant). In either case, a spherically shaped cutter is used to machine the internal geometry of the acetabulum. These spherical cutting tools are required to cut both cortical bone (hard bone) and cancellous bone (spongy bone) during normal surgery. The spherical cutter is generally assembled to a drive shaft which is coupled to a power drill and this assembly is used to machine the acetabulum for the implant. These cutters are intended for multiple surgeries and are used many times for many patients. The cutting action of these reamers is afforded by a plurality of cutting teeth. Because these teeth encounter hard bone and they are used multiple times, the cutters can become dull and inefficient in their cutting ability. Two primary problems exist with this type of instrument and surgical method:

1. Since these spherical cutters are reused, special attention is needed in properly cleaning them prior to use in preparing the next patient's acetabulum.

2. The cutting teeth can become dull even after one use and therefore do not cut bone efficiently. In addition, this cutting inefficiency generates friction/heat which can damage or kill the surrounding bone.

As these cutters become dull, they also do not cut an accurate preparation for the implant either in size or spherical geometry. Even initially, these cutters can be not accurately concentric which is further compounded by the wear and use of the cutter. Although these cutters are intended for multiple uses, there are really not quality control measures which monitor their function and eventual need to be replaced. There are not programs/qualified personnel in the hospitals that can inspect and evaluate the function and dimensional accuracy of the cutters after they have been used. It would be beneficial for the patient and the hospital to be assured that the surgeon could always be supplied with a clean/sterile spherical cutter with accurate and sharp cutting teeth for every clinical case.

Figure 1:
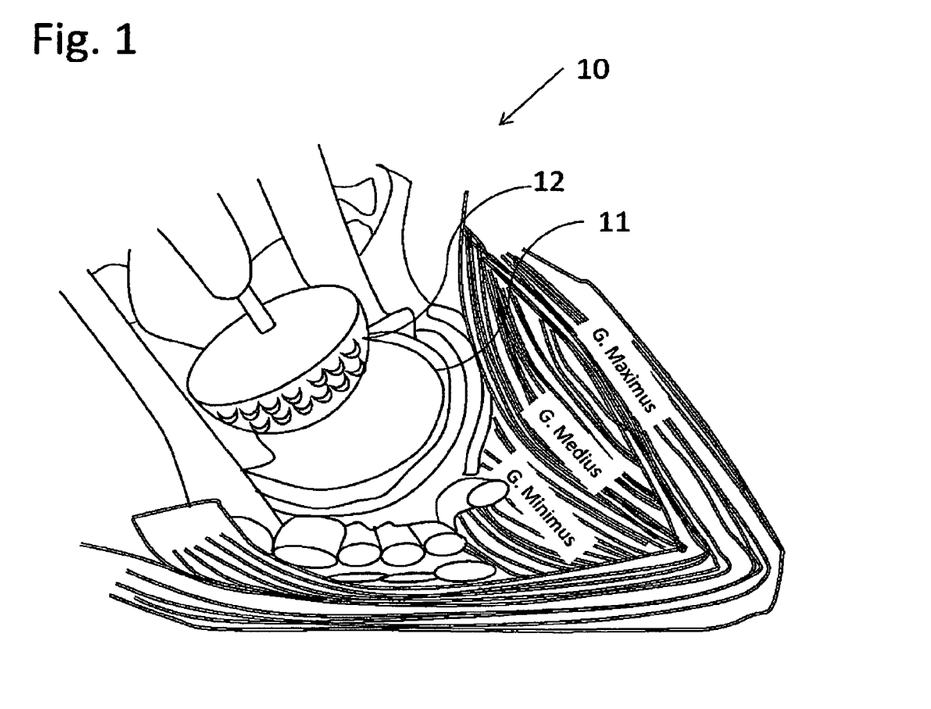
FIG. 1 Illustrates a perspective view depicting a conventional reamer found in the prior art.

Reaming of bone cavity is required during many orthopedic surgical procedures. These procedures include hip replacement and shoulder replacement and the like. Reaming of the bone cavities for the placement of an acetabular cup requires milling of precisely shaped bone cavity. When the acetabular cup is fixed by interference, this precision is more critical than when the acetabular cup is bonded to the bone cavity by a cement composition. The standard procedure for preparing a bone cavity for acetabular cup insertion using a conventional spherical reamer is illustrated in FIG. 1 at 10. The bone cavity 11 is milled by a solid reamer 12, which is generally used many times until the teeth of the spherical reamer becomes dull. Due to the presence of debris in the cutting area, the bone surface is subject to over heating and bone tissue degradation. Bone cement fragments may become included into living bone tissue creating bone healing problems.

The invention herein provides spherical hollow reamers appointed for use in medical applications. The spherical hollow reamers are disposable, so that the cutting performance is not compromised through repeated use. Several improvements towards the clinical problems seen with conventional reamers are overcome through utilization of the hollow reamers herein. Novel design features of the hollow reamer herein and improvements to conventional reamers are multifaceted and include a reusable shaft with a supporting threaded structure to precisely align a disposable, single-use spherical hollow reamer portion. The spherical hollow reamer portion is discarded after a single use to ensure a clean debris free sharp cutter for use in surgery. Moreover, when dealing with revision hip surgery, the hollow reamers have also been designed to cut bone cement (PMMA) in a more efficient manner by providing an internal space to capture the bone cement debris and thereby reducing both the cutting temperature and time required to remove the remnant cement mantle. Both these features are important in reducing heat to the bone and reducing operating room time required for revision surgery.

Figure 2:
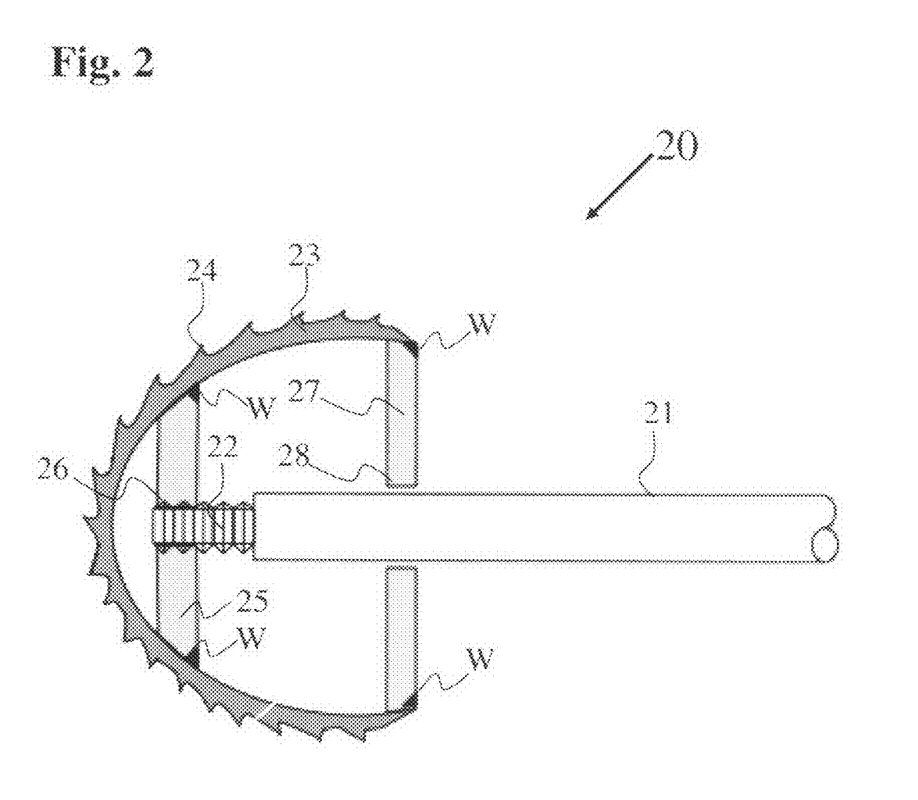
FIG. 2 depicts a cross sectional view of the assembled modular hollow spherical reamer mechanical details in accordance with the invention.

While FIG. 1 illustrates conventional reamers currently utilized, FIG. 2 illustrates at 20 a cross sectional view of an assembled disposable Spherical Hollow Reamer assembly of the present invention. The spherical hollow reamer assembly comprises at 21 a reusable shaft portion with a threaded distal end at 22. A spherical hollow reamer dome 23 with integral cutters 24 and optionally apertures (not shown) that has an interior first plate 25 welded at 'W' that has threaded aperture 26 matching the threads of the shaft 22. These threads are fine threads typically in the range of 8 to 12 thread per inch and are precision machined. A second plate 27 is welded at 'W' to the proximal circumferential end of the spherical hollow reamer dome 23 and has a central aperture 28, which is machined at a diameter suited for sliding fit on the outer diameter of the reusable shaft 21 as shown. The threaded connection between reusable shaft threads 22 and the welded first plate central threaded aperture 26 creates a first concentric attachment between the disposable spherical hollow reamer and the reusable shaft. The sliding fit between the second plate aperture 27 and the reusable shaft 21 creates a second concentric support location that is displaced from the first concentric attachment creating a solid reliable attachment of the disposable spherical hollow reamer to the reusable shaft providing concentricity and wobble free attachment even when high cutting lateral loads are applied.

Figure 3:
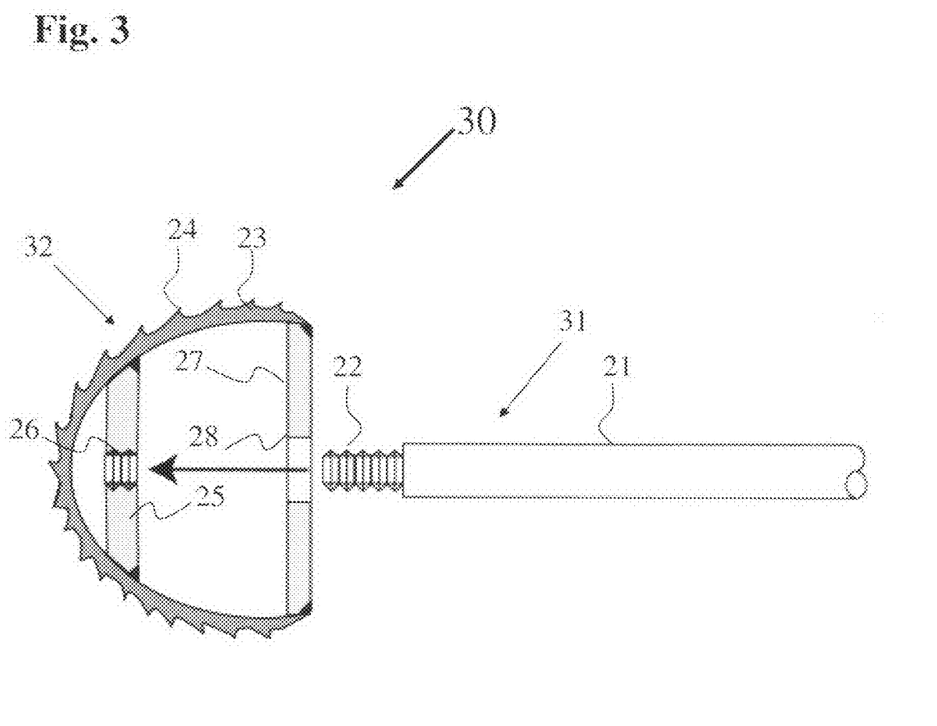
FIG. 3 depicts a cross sectional view of the disassembled modular hollow spherical reamer showing individual components of the spherical hollow reamer and the reusable shaft.

FIG. 3 illustrates at 30 a cross sectional view of the disassembled disposable Spherical Hollow Reamer assembly showing the reusable shaft 31 and the disposable hollow reamer 32. The individual parts of the reusable shaft 31 and the disposable hollow reamer 32 are numbered identical to that shown in FIG. 2.

Figure 4:
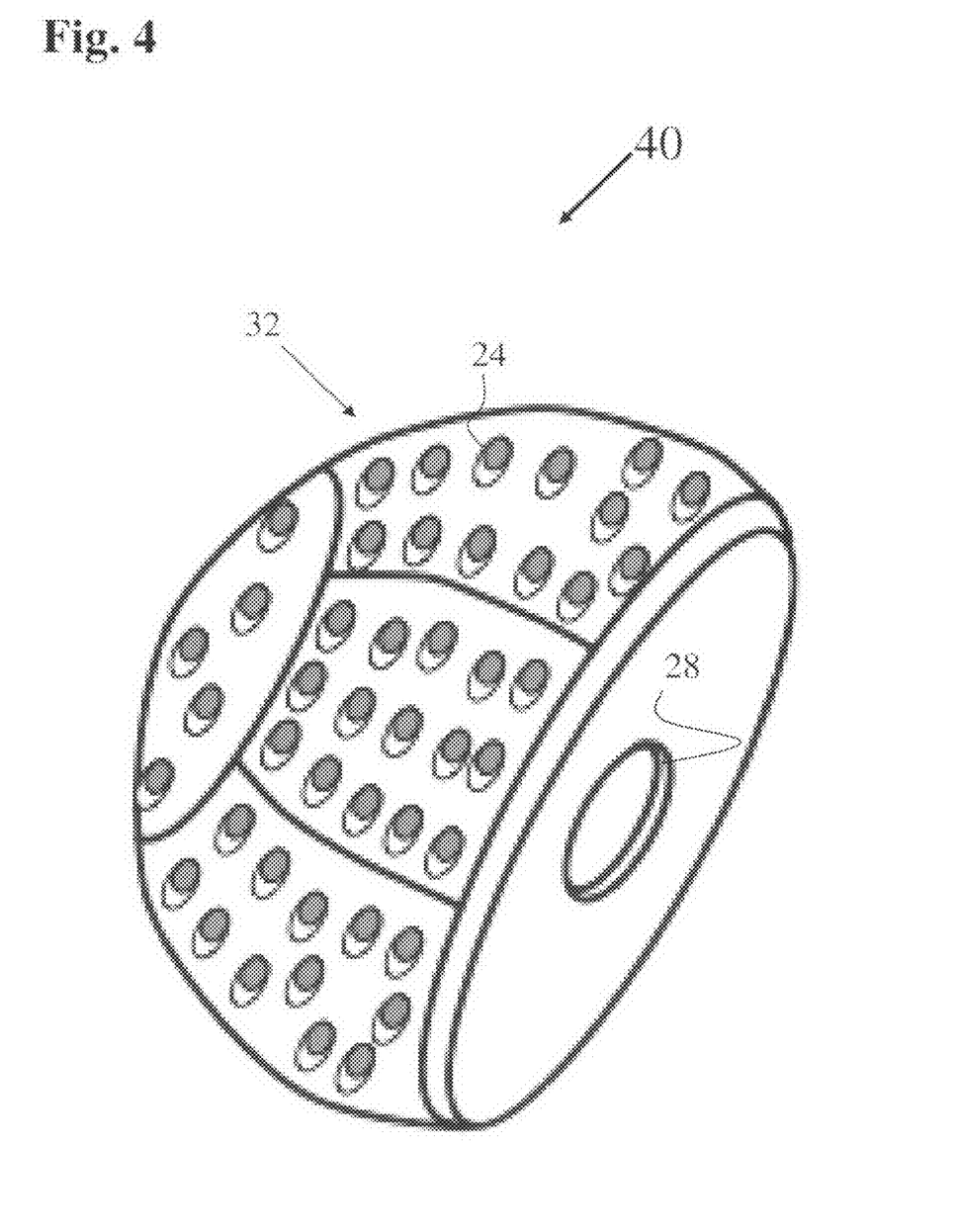
FIG. 4 is a perspective view of the modular hollow spherical hollow reamer showing the welded back plate with central aperture in accordance with the invention.

FIG. 4 illustrates at 40 a perspective view of the disposable modular hollow spherical hollow reamer showing the welded back plate with a central aperture. The disposable spherical hollow reamer 32 is available in the size range from 36 mm to 80 mm in 1 mm size increments. The disposable spherical hollow reamers have a thickness generally in the range of 0.125 mm to 0.812 mm (0.005" to 0.032"). The disposable spherical hollow reamer 32 has a sized aperture 28 which is sized to slide over the outer diameter of the reusable shaft. Groups of sizes of reamers may use a common sized aperture 28 and corresponding threaded connection 26 in the first welded plate 25 (not visible in this perspective view) mating with a single reusable shaft providing quick and easy interchange of disposable spherical hollow reamers during bone surgery.

Figure 5:
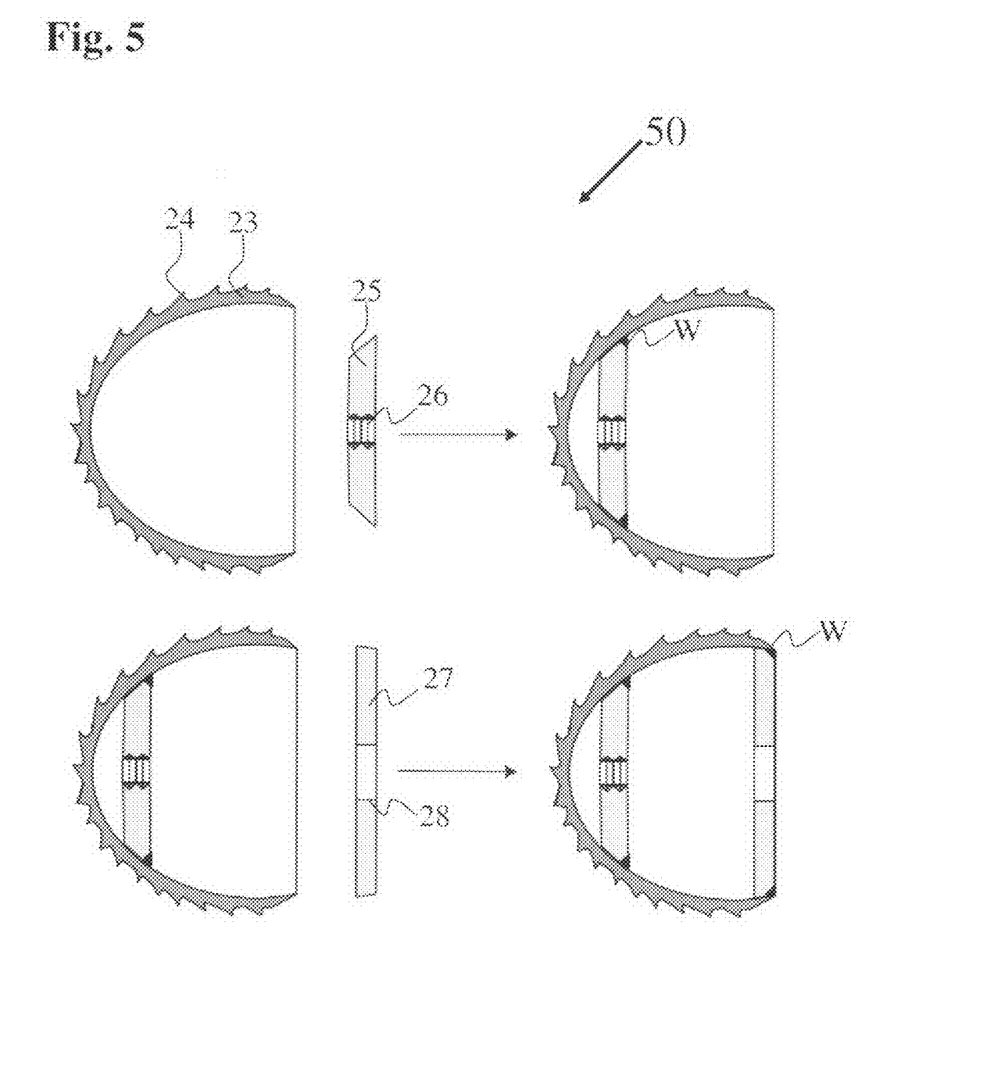
FIG. 5 depicts the steps involved in the manufacture of the spherical hollow reamer of FIG. 4.

FIG. 5 illustrates at 50 the steps involved in the manufacture of the spherical hollow reamer 32 of FIG. 4. The spherical hollow reamer dome 23 with plurality of cutters 24 is first welded to the first plate 25 with a threaded aperture 26 using laser beam welding W. The precise thread machining may be done first on the first plate 25 prior to welding or the welding operation may be done first followed by the precision machining of the threads at 26. Next the second plate 27 is laser beam welded at W. Here again, the machining of precisely dimensioned aperture 28 may be done first on the second plate 27 prior to welding or done after welding. Thus, the disposable spherical hollow reamer 32 is manufactured with precision centerline alignment with a reusable shaft.

Figure 6:
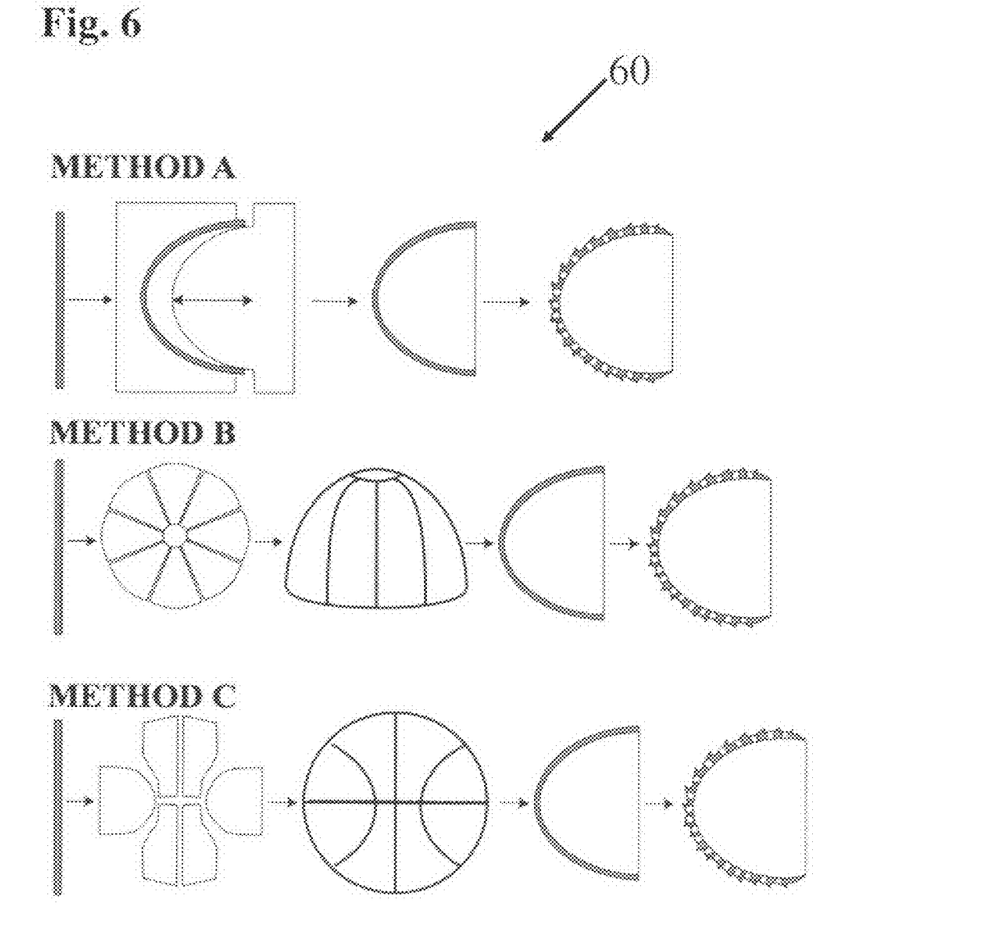
FIG. 6 depicts three alternate embodiments of the method of manufacture of spherical hollow dome of the spherical hollow reamer of FIG. 5 from a flat metallic sheet.

FIG. 6 illustrates at 60 three alternate embodiments at Method A, Method B and Method C of the method of manufacture of spherical hollow dome of the spherical hollow reamer of FIG. 5 from a flat metallic sheet. In the first embodiment of Method A, the sheet metal is pressed between two dies and the pressing action produces a spherical hollow reamer dome. The pressed hollow reamer dome is then cut with punches to produce the cutting teeth of the reamer. In the second embodiment of Method B, the flat sheet is punched into a plurality of petal shapes. Along with the cutting teeth, these petal shapes when further formed and brought together generate a nearly spherical shape. The contacting line between the petals is laser beam welded creating a nearly spherical shaped reamer dome. If necessary, the spherical shape of the dome may be optimized by a die pressing operation similar to Method A. In the third embodiment of Method C, the flat sheet is punched into a cut out shape which is similar to a basketball and at the same time each section is punched with cutting teeth. These cutout shapes are then further formed and when brought together generate a nearly spherical shape similar to a basketball. The contacting line between the cut out shapes is laser beam welded, creating a nearly spherical shaped reamer dome. If necessary, the spherical shape of the dome may be optimized by a die pressing operation similar to Method A. The family of disposable reamers addresses a wide range of bone cavity sizes, adapted to fit with corresponding reusable shafts.

Figure 7:
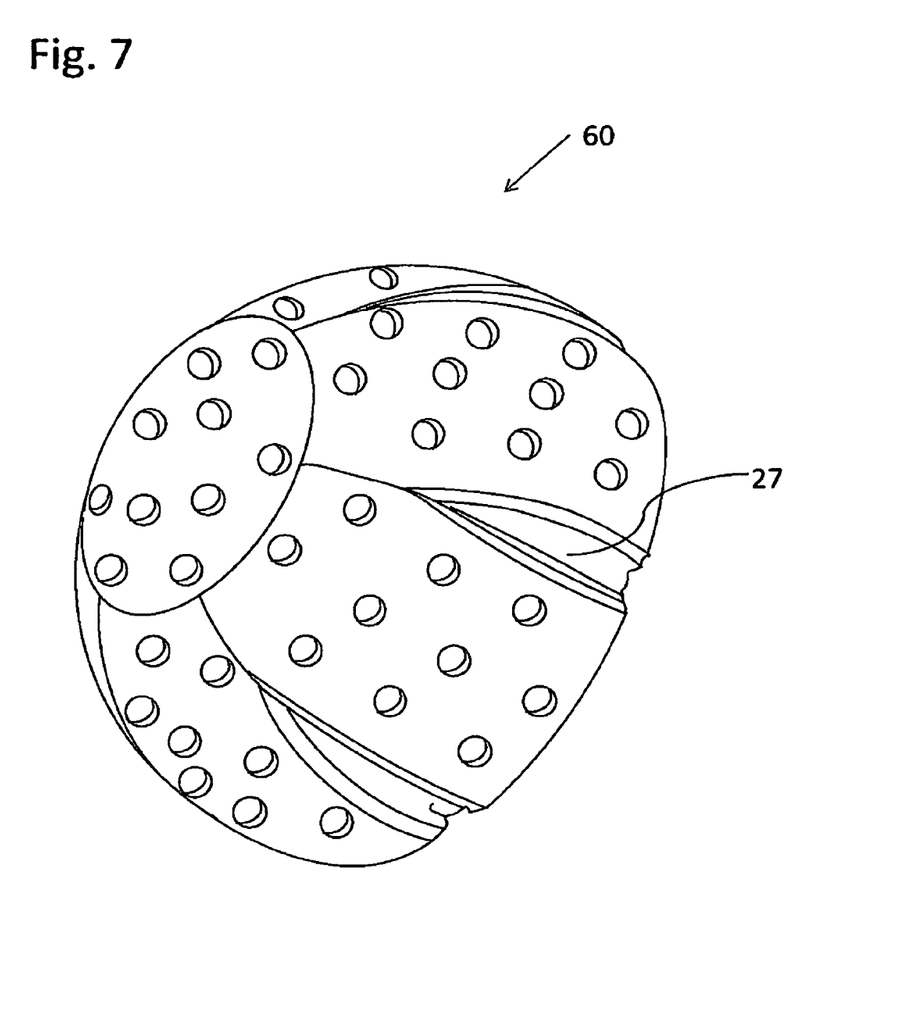
FIG. 7 is a schematic illustration of a spherical hollow dome of the spherical hollow reamer manufactured from a flat metallic sheet that is welded according to method B of FIG. 6.

FIG. 7 schematically illustrates at 70 a spherical hollow dome of the spherical hollow reamer manufactured by laser welding a cut and formed flat metallic sheet manufactured according to method B of FIG. 6. The weld line between the petals is clearly visible. Crease 71 extends from the outer edge of the spherical hollow dome which recesses inside the cutting portion of the spherical hollow reamer, thus maintaining a spherical cutting reamer body.

In some of these embodiments, the disposable spherical hollow reamer portion is provided with plurality of cutting teeth on its outer surface and a plurality of apertures for disposing bone fragments and bone cement fragments away from the reamed area thereby reducing the heat generated at the cutting interface. The spherical hollow reamer is discarded after a single use to ensure a sharp, efficient cutter for every surgery. In each of these different embodiments, the disposable spherical hollow reamer is attached to the reusable shaft using a precisely machined screw thread that engages into a corresponding threaded hole in the distal end of the reusable shaft ad the proximal end second plate slides over the outer surface of the reusable shaft. Alternately, in the embodiments described, the shaft is composed of a low cost material, and is discarded after a single use. With such an embodiment, each of the shaft and the spherical hollow reamer portions are disposable. The second plate welded to the spherical hollow reamer creates a region within the interior of the spherical reamer that captures and retains the bone fragments or bone cement debris that is discharged through the apertures adjacent to the cutters on the outer surface of the spherical hollow reamer. The spherical hollow reamer assembly provides a space for bone debris offering multiple benefits. These benefits include reducing heat generated during cutting by removing the bone debris from the outer surface of the cutter to the inside of the cutter and providing space for bone debris to be collected and later removed for bone grafting for the specific surgical procedure. The space for bone fragment accumulation is in the area between the spherical hollow reamer and the central plate provided on the reusable shaft.

The accumulated debris within the enclosed space may have bone fragments that are usable for building up bone tissue. Tapping out these bone fragments through the central aperture of the second plate may be time consuming. The second plate may optionally have two or three openings with a slidable closure plate for quick and easy removal of bone fragments and or bone cement residue. Since the openings are distributed evenly surrounding the rotational axis, the spherical hollow reamer rotates even at high rotational speeds without vibrations.

The key features of the low cost disposable spherical hollow assembly for medical applications include, in combination, the components set forth below:

a) the spherical hollow reamer assembly comprising a disposable spherical hollow reamer and a reusable shaft;
b) the reusable shaft having an elongated body with a proximal end and a distal end;
c) the proximal end having a coupling portion appointed for attachment to a drilling device;
d) the distal end having a male precision threaded portion for attachment to said disposable spherical hollow reamer;
e) the spherical hollow reamer having a spherical hollow reamer dome provided with a plurality of cutting teeth on the outer surface of the dome and a plurality of apertures for discharging bone or bone cement fragments into the interior of said spherical hollow dome;
f) a first welded plate provided in the interior portion of said spherical hollow reamer dome having a central precision threaded aperture adapted to receive the threads of the precision threaded screw at the distal end of the reusable shaft;
g) a second welded plate provided at the proximal end covering the edges of the spherical hollow reamer dome having a center precision diameter aperture that slides over the outer diameter of the reusable shaft;

whereby the screwed attachment of said disposable spherical hollow reamer to the reusable shaft distal end aligns their centerlines at a first alignment location and the sliding action of the second plate central aperture over the outer diameter of the reusable provides a second alignment location displaced from the first alignment location, thereby preventing wobbliness during reaming and creating precise bone cavities that replicate the spherical shape of the disposable spherical hollow reamer in a medical procedure while the containment volume between the interior of the spherical hollow reamer and the second plate captures bone fragment or bone cement fragment.

The manufacturing process for the spherical hollow reamer dome of the disposable spherical hollow reamer comprises the following manufacturing steps;
 a) In the first method, Method A, a flat sheet of the reamer material is selected and pressed between a spherical dome die set to generate the precise spherical hollow reamer dome shape and cutting teeth are produced by punching operation;
 b) In the second method, Method B, a flat sheet of reamer material is stamped into a plurality of petal shapes with cutting teeth, which form a nearly spherical shape when the edges of the adjacent petals are brought together. These contacting edges are welded, preferably by laser beam welding which does not additional material at the weld site. If necessary, the welded spherical hollow reamer dome may be pressed in a die set similar to Method A, creating a true spherical shape;
 c) In the third method, Method C, a flat sheet of reamer material is stamped into shape resembling basketball cutouts with cutting teeth, which form a nearly spherical basketball like shape when the edges of the adjacent shapes are brought together. These contacting edges are welded, preferably by laser beam welding which does not additional material at the weld site. If necessary, the welded spherical hollow reamer dome may be pressed in a die set similar to Method A, creating a true spherical shape.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A disposable low cost acetabular spherical hollow reamer assembly for medical applications, comprising:
 a. a disposable spherical hollow reamer and a reusable shaft;
 b. said reusable shaft having an elongated body with a proximal end and a distal end, said proximal end having a coupling portion appointed for attachment of said spherical hollow reamer assembly to a drilling device, said distal end having a male precision threaded portion for attachment to said disposable spherical hollow reamer;
 c. a disposable spherical hollow reamer, comprising:
  1. a disposable spherical hollow reamer dome having a hollow construction with an outer surface, an interior surface and a bone debris capturing cavity, said outer surface further comprising a plurality of cutting teeth and a plurality of apertures;
  2. said disposable spherical hollow reamer dome having an internal welded first plate with female precision threaded aperture centrally located within said bone debris capturing cavity of said spherical hollow reamer dome adapted to receive said male precision threaded portion of the distal end of the reusable shaft;
  3. said disposable spherical hollow reamer dome having an external welded second plate at the proximal end with a centrally located precision diameter aperture adapted to slide over the outer diameter of the reusable shaft with a sliding fit tolerance;
  whereby a screwed attachment of said disposable spherical hollow reamer welded first plate to the reusable shaft distal end aligns their centerlines at a first attachment location and the sliding fit of the aperture in the welded second plate over the outer diameter surface of the reusable shaft provides a second attachment location that is displaced from the first attachment location, preventing wobbliness during reaming and creating precise bone cavities that replicate the shape of the disposable spherical hollow reamer in a medical procedure, and the second welded plate of the spherical hollow reamer in combination with the spherical hollow reamer interior surface forms a containment volume for capturing bone fragment or bone cement fragment.

2. A reamer for medical applications as recited by claim 1, wherein said disposable spherical hollow reamer has an outer surface diameter in the range of 36 mm to 80 mm.

3. A reamer for medical applications as recited by claim 1, wherein said spherical hollow reamer dome is made from a thin sheet of reamer material.

4. A reamer for medical applications as recited by claim 3, wherein said thin sheet of reamer material is stainless steel.

5. A reamer for medical applications as recited by claim 3, wherein said thin sheet of reamer material has a thickness ranging from 0.125 mm to 0.812 mm.

6. A reamer for medical applications as recited by claim 1, wherein said welded first plate and welded second plate are welded to said spherical hollow reamer dome by laser beam welding.

7. A reamer for medical applications as recited by claim 1, wherein said spherical hollow reamer dome and said welded second plate forming an enclosed space for collecting bone fragments and bone cement debris.

8. A reamer for medical applications as recited by claim 1, wherein said disposable spherical hollow reamer is easily assembled.

9. A reamer for medical applications as recited by claim 1, wherein said threaded portion of said distal end of said shaft portion has a right-hand male thread for assembly into said welded first plate having a right handed female thread.

10. A reamer for medical applications as recited by claim 1, wherein said elongated body of said shaft portion further comprises a plurality of graduations to determine the depth of said disposable spherical hollow cutter assembly in the bone cavity during use.

11. A reamer for medical applications as recited by claim 1, wherein said elongated body of said shaft portion further comprises a marking to indicate its size.

12. A reamer for medical applications as recited by claim 1, wherein said spherical hollow reamer further comprises a marking to indicate its size.

13. A reamer for medical applications as recited by claim 1, wherein said disposable spherical hollow reamer is appointed for a single, one-time use.

14. A reamer for medical applications as recited by claim 1, wherein said shaft portion is solid.

15. A reamer for medical applications as recited by claim 1, wherein said shaft portion is flexible.

* * * * *